United States Patent
Bashiri et al.

[11] Patent Number: 6,165,178
[45] Date of Patent: Dec. 26, 2000

[54] FAST DETACHING ELECTRICALLY ISOLATED IMPLANT

[75] Inventors: Mehran Bashiri, San Carlos; Michael P. Wallace, Pleasanton; Pete Phong Pham, Fremont; Cong Thach, Fremont; Chad C. Roue, Fremont; Joseph C. Eder, Los Altos Hills; Erik T. Engelson, Menlo Park, all of Calif.

[73] Assignee: SCIMED Life Systems, Inc., Maple Grove, Minn.

[21] Appl. No.: 09/144,950

[22] Filed: Sep. 1, 1998

Related U.S. Application Data

[63] Continuation-in-part of application No. 08/941,458, Sep. 30, 1997, Pat. No. 5,984,929, which is a continuation-in-part of application No. 08/921,407, Aug. 29, 1997, abandoned.

[51] Int. Cl.[7] ....................................................... A61F 11/00
[52] U.S. Cl. .................................................. 606/108; 606/1
[58] Field of Search ................................... 606/108, 151, 606/198, 191, 194, 200, 1, 157; 128/898

[56] References Cited

U.S. PATENT DOCUMENTS

| | | |
|---|---|---|
| 4,010,759 | 3/1977 | Boer . |
| 4,739,768 | 4/1988 | Engelson . |
| 4,884,579 | 12/1989 | Engelson . |
| 4,945,342 | 7/1990 | Steinemann . |
| 4,994,069 | 2/1991 | Ritchart et al. . |
| 5,122,136 | 6/1992 | Guglielmi et al. . |
| 5,234,437 | 8/1993 | Sepetka . |
| 5,250,071 | 10/1993 | Palermo . |
| 5,261,916 | 11/1993 | Engelson . |
| 5,304,195 | 4/1994 | Twyford, Jr. et al. . |
| 5,312,415 | 5/1994 | Palermo . |
| 5,350,397 | 9/1994 | Palermo et al. . |
| 5,354,295 | 10/1994 | Guglielmi et al. . |
| 5,423,829 | 6/1995 | Pham et al. . |
| 5,522,836 | 6/1996 | Palermo . |
| 5,540,680 | 7/1996 | Guglielmi et al. . |
| 5,582,619 | 12/1996 | Ken .......................................... 606/191 |
| 5,624,449 | 4/1997 | Pham et al. . |
| 5,632,771 | 5/1997 | Boatman et al. ......................... 606/198 |
| 5,649,951 | 7/1997 | Davidson . |
| 5,733,294 | 3/1998 | Forber et al. . |
| 5,743,905 | 4/1998 | Eder et al. . |
| 5,800,454 | 9/1998 | Jacobsen et al. . |
| 5,855,578 | 1/1999 | Guglielmi et al. . |
| 5,891,128 | 4/1999 | Gia et al. ................................... 606/1 |
| 5,891,130 | 4/1999 | Palermo et al. ............................ 606/1 |
| 5,895,385 | 4/1999 | Guglielmi et al. . |
| 5,895,391 | 4/1999 | Farnholtz . |
| 5,911,717 | 6/1999 | Jacobsen et al. . |
| 5,916,235 | 6/1999 | Guglielmi . |
| 5,919,187 | 7/1999 | Guglielmi et al. . |
| 5,925,037 | 7/1999 | Guglielmi et al. . |
| 5,925,060 | 7/1999 | Forber . |
| 5,925,062 | 7/1999 | Purdy . |
| 5,928,226 | 7/1999 | Guglielmi et al. . |
| 5,944,714 | 8/1999 | Guglielmi et al. . |
| 5,984,929 | 11/1999 | Bashiri et al. ........................... 606/108 |

FOREIGN PATENT DOCUMENTS

| | | |
|---|---|---|
| 0 719 522 A1 | 7/1996 | European Pat. Off. . |
| WO 97/48351 | 12/1997 | WIPO . |
| WO 98/02100 | 1/1998 | WIPO . |
| WO 98/04198 | 2/1998 | WIPO . |
| WO 98/04315 | 2/1998 | WIPO . |

*Primary Examiner*—Michael Buiz
*Assistant Examiner*—Kevin Truong
*Attorney, Agent, or Firm*—Morrison & Foerster LLP

[57] ABSTRACT

This is an implant for placement in the human body and an assembly for so placing that implant. Most desirably, it is an implant for use in the vasculature of the human body and is used to occlude some space in that vasculature as a portion of a treatment regimen. The implant itself is preferably a component of a deployment device using an electrolytically severable joint. The implant is electrically isolated from the electrolytically severable joint by a highly resistive or insulative layer. Such isolation and minimization of the conductive pathway from the placement apparatus to the body's fluids appears to enhance the susceptibility of the electrolytic joint to quick erosion and detachment of the implant from the deployment media. Although the implant itself is preferably a vaso-occlusive device, it may instead be a stent, a vena cava filter, or other implant which may be installed in this manner.

32 Claims, 12 Drawing Sheets

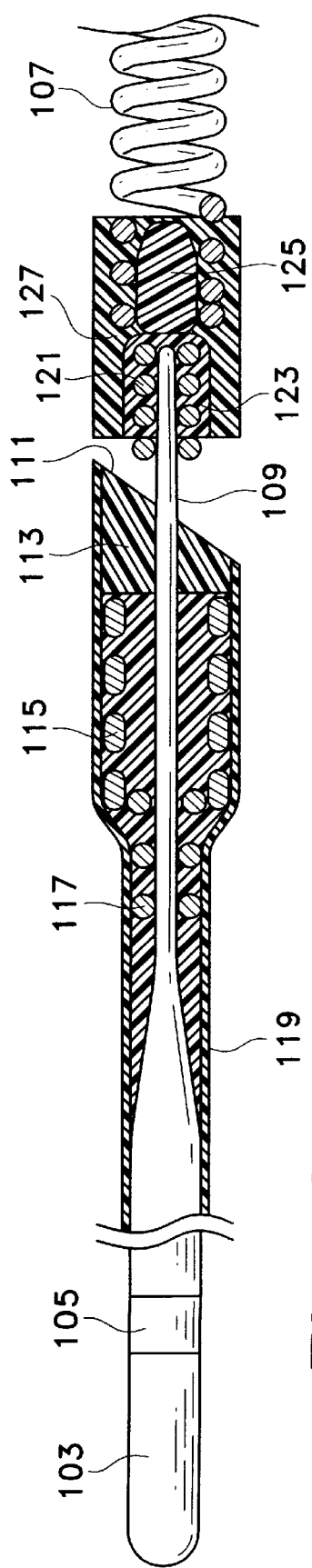
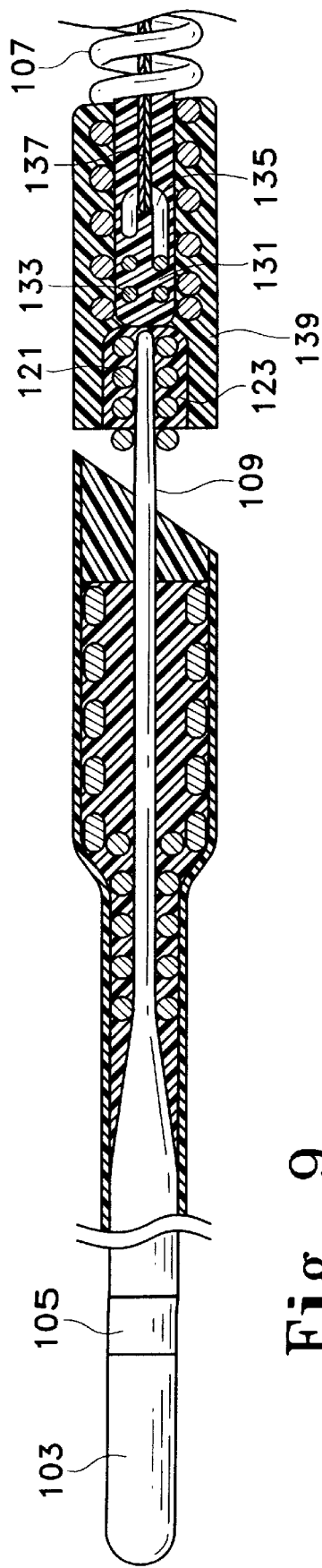
Fig. 8
Fig. 9

FAST DETACHING ELECTRICALLY ISOLATED IMPLANT

RELATED APPLICATIONS

This is a continuation in part of U.S. Ser. No. 08/941,458, filed Sep. 30, 1997, now U.S. Pat. No. 5,984,929 which is a continuation-in-part of U.S. Patent Application Serial No. 08/921,407, filed Aug. 29, 1997, now abandoned, the entirety of which are incorporated by reference.

FIELD OF INVENTION

This invention is an implant for placement in the human body and an assembly for so placing that implant. Most desirably, it is an implant for use in the vasculature of the human body and is used to occlude some space in that vasculature as a portion of a treatment regimen. The implant itself is preferably a component of a deployment device or assembly using an electrolytically severable joint. The implant is electrically isolated from the electrolytically severable joint by a highly resistive or insulative layer. Such isolation and minimization of the conductive pathway from the placement apparatus to the body's fluids appears to enhance the susceptibility of the electrolytic joint to quick erosion and detachment of the implant from the deployment media. Although the implant itself is preferably a vaso-occlusive device, it may instead be a stent, a vena cava filter, or other implant which may be installed in this manner.

BACKGROUND OF THE INVENTION

Implants may be placed in the human body for a wide variety of reasons. For instance, stents are placed in a number of different lumens in the body. They may be placed in arteries to cover vascular lesions or to provide patency to the vessel. Stents are also placed in biliary ducts to prevent them from kinking or collapsing. Grafts may be used with stents to promote growth of endothelial tissue within those vessels.

Vena cava filters are implanted in the body, typically in the vena cava, to catch thrombus which are sloughed off from other sites within the body and which may be in the blood passing through the chosen site.

Vaso-occlusive devices or implants are used for a wide variety of reasons. They are often used for treatment of intra-vascular aneurysms. This is to say that the treatment involves the placement of a vaso-occlusive device in an aneurysm to cause the formation of a clot and eventually of a collagenous mass containing the vaso-occlusive device. These occlusions seal and fill the aneurysm thereby preventing the weakened wall of the aneurysm from being exposed to the pulsing blood pressure of the open vascular lumen.

Treatment of aneurysms in this fashion is a significant improvement over the surgical method typically involved. The surgical or extravascular approach is a common treatment of intra-cranial berry aneurysm; it is straightforward but fairly traumatic. The method involves removing of portion of the cranium and locating the aneurysm. The neck of the aneurysm is closed typically by applying a specially sized clip to the neck of the aneurysm. The surgeon may choose to perform a suture ligation of the neck or wrap the entire aneurysm. Each of these procedures is performed by an very intrusive invasion into the body and is performed from the outside of the aneurysm or target site. General anesthesia, craniotomy, brain retraction, and a placement of clip around the neck of the aneurysm all are traumatic. The surgical procedure is often delayed while waiting for the patient to stabilize medically. For this reason, many patients die from the underlying disease prior to the initiation of the surgical procedure.

Another procedure—the extra-intravascular approach—involves surgically exposing or stereotaxically reaching an aneurysm with a probe. The wall of the aneurysm is perforated from the outside and various techniques are used to occlude the interior of the aneurysm to prevent its rebleeding. The techniques used to occlude the aneurysm include electro-thrombosis, adhesive embolization, hoghair embolization, and ferromagnetic thrombosis. These procedures are discussed in U.S. Pat. No. 5,122,136 to Guglielmi et al., the entirety of which is incorporated by reference.

Guglielmi et al. further describes an endovascular procedure which is at once the most elegant and least invasive. The procedure described in that patent includes a step in which the interior of the aneurysm is entered by the use of guidewire such as those in Engelson, U.S. Pat. No. 4,884,579 and a catheter as in Engelson, U.S. Pat. No. 4,739,768. These patents described devices utilizing guidewires and catheters which allow access to aneurysms from remote parts of the body. Typically, these catheters enter the vasculature through the femoral artery in the groin. The Guglielmi et al. system uses catheters and corewires which have a very flexible distal regions and supporting midsections which allow the combinations to be steerable to the region of the aneurysm. That is to say that the guidewire is first steered for a portion of the route to the aneurysm and the catheter is slid up over that guidewire until it reaches a point near the distal end of the guidewire. By steps, the catheter and guidewire are then placed at the mouth of the aneurysm. The catheter is introduced into the aneurysm and vaso-occlusive or embolism-forming devices may be delivered through the lumen.

Various vaso-occlusive devices are introduced through the noted microcatheters to close the aneurysm site. In some instances, a small balloon may be introduced into the aneurysm where it is inflated, detached, and left to occlude the aneurysm. Balloons are becoming less in favor because of the difficulty in introducing the balloon into the aneurysm sac, the possibility of aneurysm rupture due to over-inflation of the balloon within the aneurysm, and the inherent risk associated with the traction produced when detaching the balloon.

Another desirable embolism-forming device which may be introduced into aneurysm using end of vascular placement procedure is found in U.S. Pat. No. 4,994,069 to Ritchart et al. In that patent are described various devices—typically platinum/tungsten alloy coils having very small diameters—which may be introduced into the aneurysm through a catheter such as those described in the Engelson patents above. These coils are often made of wire having a diameter of 2–6 mils. The coil diameter is often 10–30 mils. These soft, flexible coils, may be of any length desirable and appropriate for the site to be occluded. After these vaso-occlusive coils are placed in, e.g., a berry aneurysm, they first cause a formation of an embolic mass. This initial mass is shortly thereafter complemented with a collagenous material which significantly lessens the potential for aneurysm rupture.

There are variety of other vaso-occlusive devices, typically coils which may be delivered to the vascular site in a variety of ways, e.g., by mechanically detaching them from the delivery device. A significant number of these devices are described in patents owned by Target Therapeutics, Inc. For instance:

U.S. Pat. No. 5,234,437 to Sepetka, which shows a method of unscrewing a helically wound coil from a pusher having interlocking surfaces.

U.S. Pat. No. 5,250,071 to Palermo, which shows an embolic coil assembly using interlocking clasps both on the pusher and on the embolic coil.

U.S. Pat. No. 5,261,916 to Engelson, which shows a combination pusher/vaso-occlusive coil assembly joined by an interlocking ball and keyway type coupling.

U.S. Pat. No. 5,304,195 to Twyford et al., shows a pusher/vaso-occlusive coil assembly having a fixed proximally extending wire carrying a ball on its proximal end and a pusher having a similar end which two tips are interlocked and disengaged when expelled from the distal tip of the catheter.

U.S. Pat. No. 5,312,415, to Palermo shows a method for discharging numerous coils from a single pusher by using a guidewire which has a section capable of interconnecting with the interior of a helically wound coil.

U.S. Pat. No. 5,350,397, to Palermo et al. shows a pusher having a throat at its distal end and a pusher through its axis. The pusher throat holds onto the end of an embolic coil and releases that coil upon pushing the axially placed pusher wire against member found on the proximal end of the vaso-occlusive coil.

Other mechanically detachable embolism forming devices are known in the art.

Each of the patents listed herein is specifically incorporated by reference.

Guglielmi et al. shows an embolism forming device and procedure for using that device which, instead of a mechanical joint, uses an electrolytically severable joint. Specifically, Guglielmi et al. desirably places a finely wound platinum coil into a vascular cavity such as an aneurysm. The coil is delivered endovascularly using a catheter such as those described above. After placement in the aneurysm, the coil is severed from its insertion core wire by the application of a small electric current to that core wire. The deliverable coils are said to be made of a platinum material. They may be 1–50 cm or longer as is necessary. Proximal of the embolic coil, as noted above, is a core wire which is typically stainless steel. The core wire is used to push the platinum embolic coil into vascular site to be occluded.

Other variations of the Guglielmi et al. technology are found in U.S. Pat. No. 5,354,295.

None of the references described above teaches or suggest an implant assembly having a highly resistive or insulative joint between that implant and a cooperating electrolytically severable delivery joint.

SUMMARY OF THE INVENTION

This invention is an implant assembly in which an implant is placed in the human body using an electrolytically severable joint. The implant is isolated from the electrical circuit within the body by an insulative or high resistance member. The implant may be a vaso-occlusive device, stent, vena cava filter, or any other implant which may be delivered via a catheter. Desirably, the device includes a core wire having a distal tip, which distal tip or implant may be introduced into the selected site. The core wire is attached to the distal tip or implant in such a way that the implant may be electrolytically detached by application of a current to the core wire.

The improvement involves the use of an insulative or highly resistive member proximal of the implant. The resistive or insulating member may be any suitable material such as inorganic oxides, glues, polymeric inserts, polymeric coverings, etc. This insulative or highly resistive layer or joint appears to focus the current flow through the sacrificial electrolytic joint and thereby improves the rate at which detachment of the implant occurs.

BRIEF DESCRIPTION OF THE DRAWINGS

FIGS. 2–11 show respectively cross sections depicting various insulating or resistive joints which electrically isolate implants.

DESCRIPTION OF THE INVENTION

As noted above, the Guglielmi et al. system for deploying an implant into the human body uses a core wire, an electrolytic sacrificial joint, and the implant to be deployed. A power supply is needed to provide power for electrolysis of the joint. The core wire is typically insulated on its outer surface from near the proximal end of the wire and along the wire to the electrolytic sacrificial joint. The implant typically forms a portion of the circuit through the body. This invention substantially removes the implant itself from that circuit thereby apparently focusing the current flow at the electrolytic joint where it is needed for electrolysis.

Figure 1:
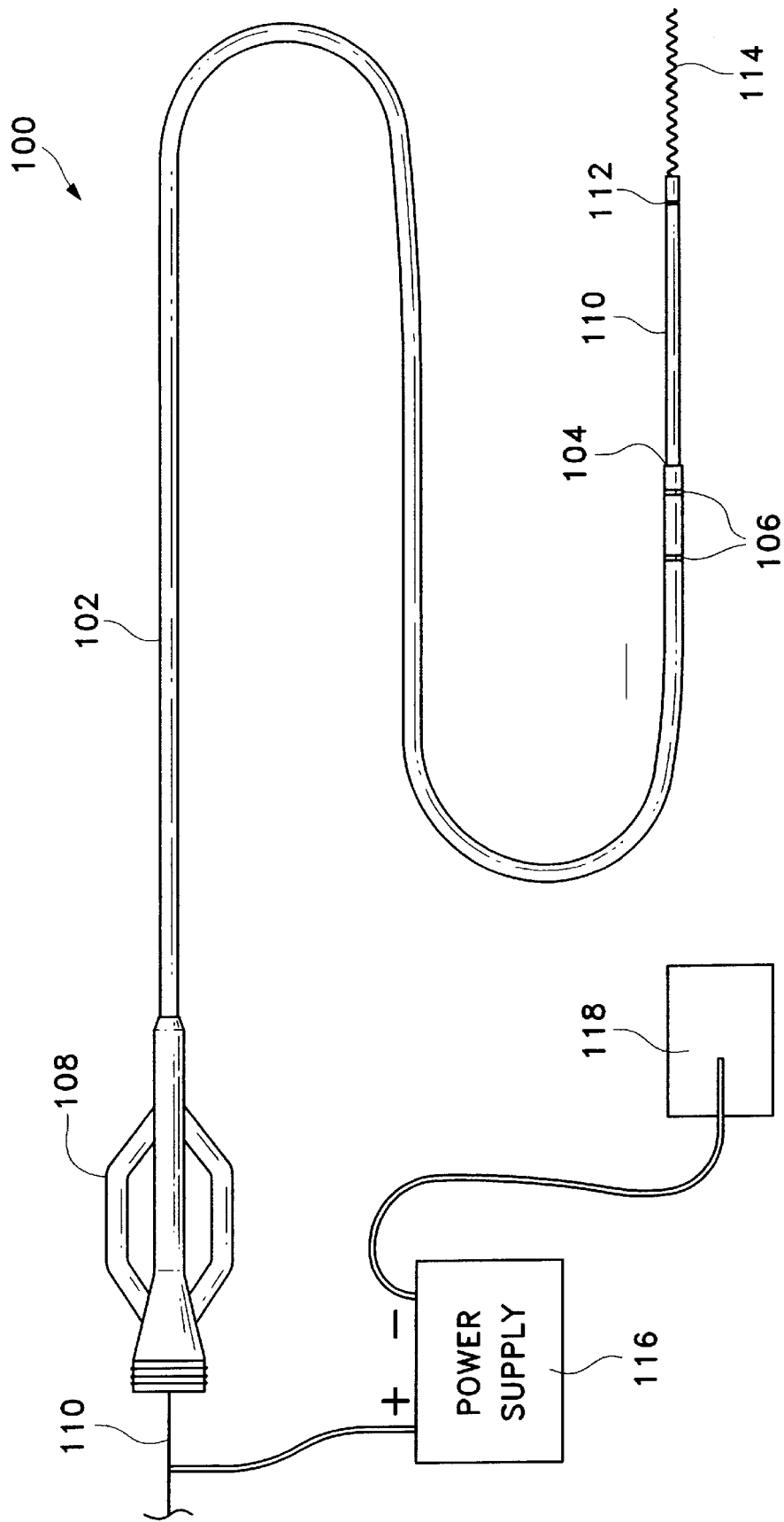
FIG. 1 shows the overall layout of delivery system showing the typical major parts for delivering an implant using the improvement of this invention.

FIG. 1 shows a system for introducing and deploying the implant made according to the invention. The system (100) includes a catheter (102) which is made up of an elongate tubular member, typically made from a polymeric material and often reinforced with a coil or braid to provide strength or obviate kinking propensities. Catheter (102) is shown with a pair of radiopaque markers (106). The radiopaque markers (106) allow visualization of the distal end (104) of the catheter so to compare it with the coincidence of the implant. Catheter (102) is also shown with a proximal fitting (108) for introduction of dyes or treatment materials. Within the lumen of catheter (102) is a core wire (110) extending both proximally of catheter (102) and distally. On the distal end of core wire (110) may be seen the electrolytic joint (112) and the implant (114). In this instance, implant (114) is shown to be a helically wound vaso-occlusive coil. Generally, all of core wire (110) is electrically insulated from a point near the proximal end of core wire (110) continuously to electrolytically severable joint (112). Electrolytically severable joint (112) is bare and is relatively more susceptible to electrolysis in an ionic solution such as blood or most other bodily fluids than is the implant (114).

The most proximal end of core wire (110) is also left bare so that power supply (116) may be attached. The other pole of the power supply (116) is typically attached to a patch (118). The patch is placed on the skin to complete the circuit from the power supply (116), through the core wire (110), through electrolytic joint (112), through the ionic solution in the body, and back to a patch (118) to the power supply (116). Other return routes may be used as the designer sees fit.

Central to this invention is electrical isolation of implant (114) from core wire (110) and electrolytically severable joint (112). Without wishing to be bound by theory, it is believed that isolation of the implant (114) prevents or lessens current flow through the implant (114) itself and concentrates the current flow through the electrolytic joint (112).

Figure 2:
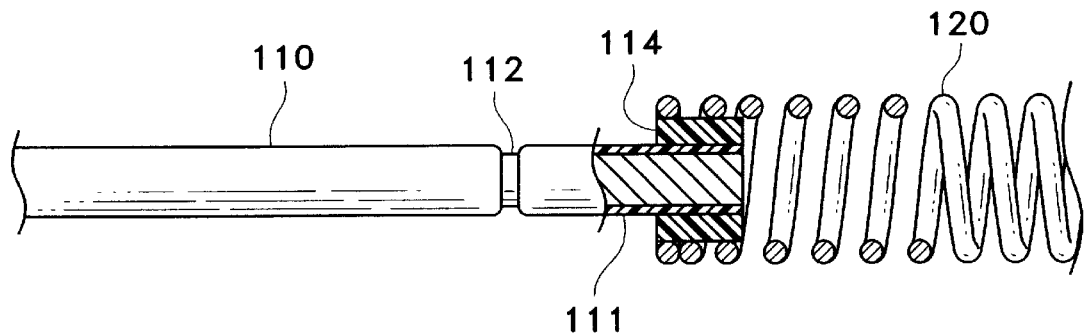

FIG. 2 shows a close-up of the more distal portion of one variation of the invention. This variation includes the core wire (110) and the attached implant (120). Typically, core wire (110) will be conductive but covered with a insulative layer (111) both proximal and distal of electrolytically severable joint (112). The interior of core wire (110) is physically attached to implant (120). In this variation of the invention, implant (120) is a helically wound coil.

In this invention, a highly resistive or insulative layer or member electrically isolates implant (120) from core wire (110). In this variation of the invention, the insulating layer (111) on the core wire (110) is simply continued to the end of the core wire (110). An optional bushing (114) is placed on the core wire (110) to further separate it from implant (120). Optional bushing (114) may be of any suitable material since it operates merely as a spacer. Insulating layer (111) may be polytetrafluoroethylene (e.g., Teflon), polyparaxylylene (e.g., parylene), polyethyleneterephthalate (PET), polybutyleneterephthalate (PBT), cyanoacrylate adhesives, or other suitable insulating layer, but preferably is polymeric and most preferably is PET.

The coil making up this variation (and other coil-based variations) of the invention is generally of a diameter in the range of 0.025 inches and 0.006 inches. Wire of such diameter is wound into a primary form having a diameter of between 0.003 and 0.025 inches. For most neurovascular indications, the preferable primary coil diameter is preferably between 0.008 and 0.018 inches.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Figure 3:
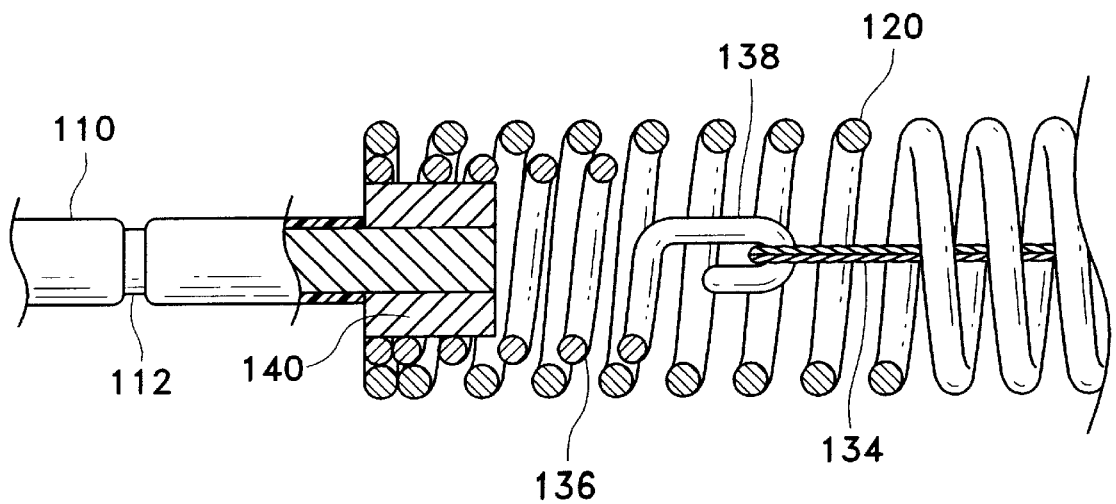

FIG. 3 shows a close-up of another variation of the invention including the more distal portion of the core wire (110) and the attached implant (120). In this variation of the invention, implant (120) is a helically wound coil having a stretch-resistant member (134) through its center lumen. The anti-stretch member (134) may be of any suitable material, e.g., metallic wire or polymeric threads. Preferred are polymeric threads comprised of a member selected from the group consisting of polyethylene, polypropylene, polyamides, and polyethyleneterephthalate although almost any polymeric material which is formable into a fiber is quite suitable. The stretch-resistant member is simply designed to prevent the coil (120) from stretching in the event that core wire (110) must be withdrawn or repositioned to change the position of the implant (120).

The stretch-resistant member (134) is attached to an interior anchor coil (136) having a distal hook (138) to which the stretch-resistant member (134) is attached. An optional bushing (140) is present and attached to the metallic center of the core wire (110). In this variation of the invention, either or both of the optional bushing (140) or interior anchor coil (136) may be of an oxide-forming material such as tantalum and the like. We have found that when tantalum or other such refractory forming materials are subjected to welding operations as may be found when assembling this device, an apparently oxidic, but highly electrically resistive layer is formed at the junction of the tantalum and its neighbor.

Figure 4:
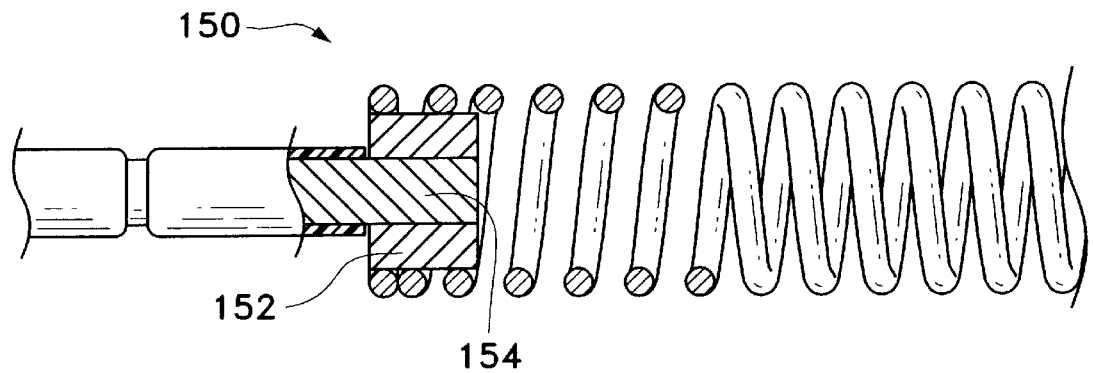

FIG. 4 shows another variation (150) of the inventive implant assembly. In this variation, bushing (152) is formed of an oxidic or insulative-forming material and is included to form such a resistive layer during operations to weld the metallic center (154) to bushing (152).

Figure 5:
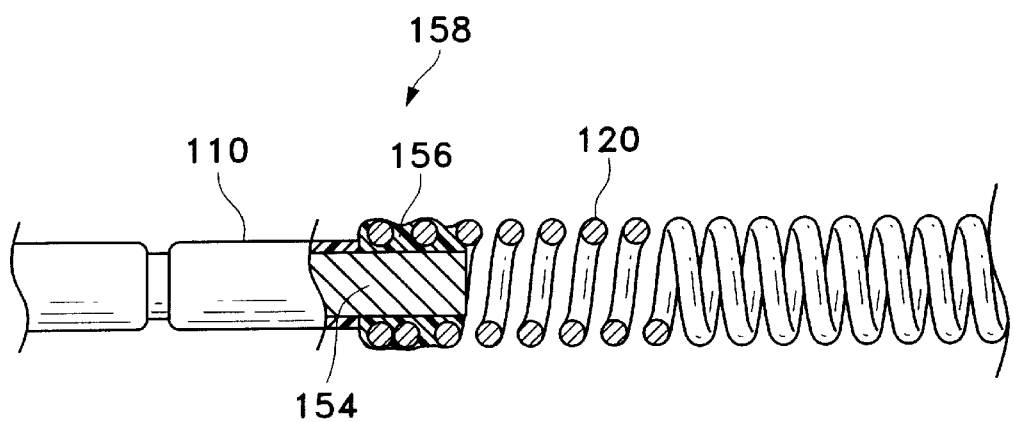

FIG. 5 shows another variation (158) of the inventive implant assembly. In this variation, the implant (120) is attached to the core wire (110) and at the same time is electrically insulated from the metallic center (154) of core wire (110) by the use of a glue or thermopolymer (156) made from a suitable polymer, e.g., a thermoplastic, preferably comprising a member selected from the group consisting of polyethylene, polypropylene, polyamides, and polyethyleneterephthalate.

An "oxide forming material" or "insulator-forming material" as those terms are used herein are materials which, under the imposition of an appropriate electrical current or other such excitation, will form an insulating, preferably oxide, layer. One such material is the metal tantalum and certain of its alloys. Other insulation forming materials or oxide forming materials include zirconium.

Although the use of solid insulation forming material is shown in FIGS. 3 and 4, the use of an insulation forming material in a layer is also contemplated. Such a layer may be plated, sputtered, painted, heat shrunk, glued, or melted onto the appropriate part.

Figure 6:
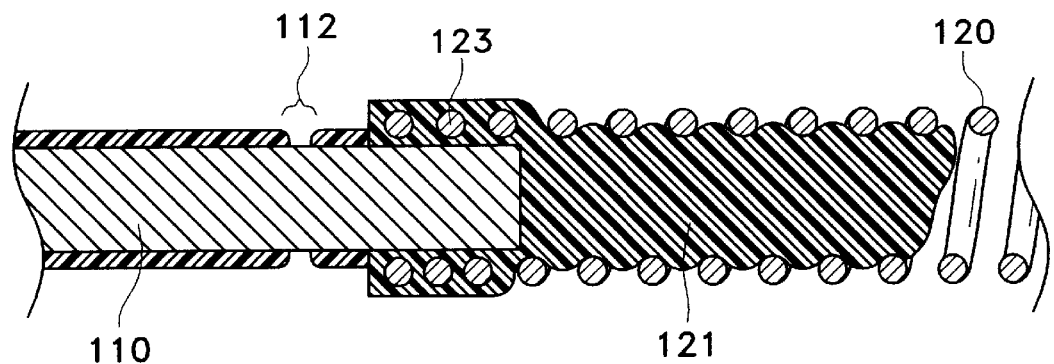
Figure 7:
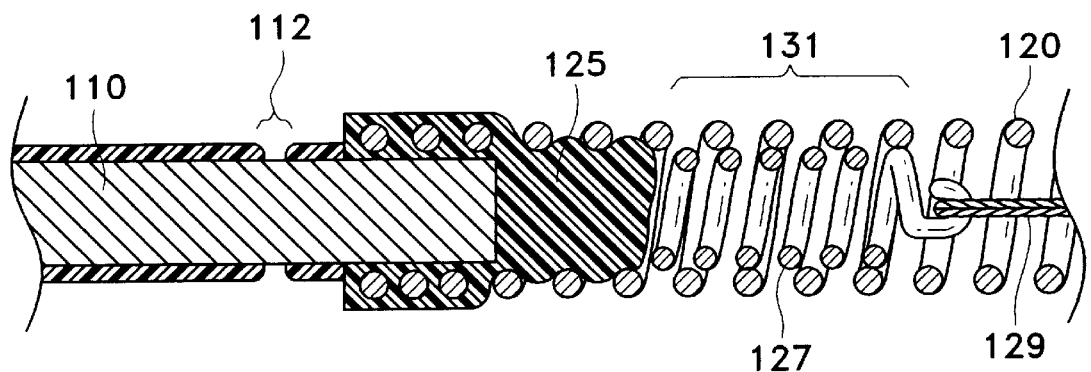

FIG. 6 shows another variation of the invention, in this case using a polymeric insert between core wire (110) and helical deployment coil (120). Electrolytically severable joint (112) is also shown. The polymeric insert (121) typically includes a radiopaque marker coil (123) and is simply slid over the distal tip of core wire (110) and into the lumen of helical coil (120). Once so assembled, this assemblage is heat-treated to cause the various portions to adhere to each other. As is the case with any of the other variations shown herein, it may be desirable to place circumferential ribs on the distal tip of core wire (110) to provide a more suitable bond for the polymeric insert (121). Care must be taken, of course, to ensure that polymeric plug (121) contains no materials (e.g., dyes or opacifiers) which would enhance the conductivity of the plastic. It is the task of polymeric insert (121) to insulate core wire (110) from deployable helical coil (120) so the electrolytic joint (112) is easily and readily detached. It should be noted, that although the radiopaque coil (123) is highly desirable, in this invention, it is completely optional.

FIG. 6 shows still another variation of the invention. This variation is a similar concept both to the polymeric plug variation shown in FIG. 8 and to the variation shown in FIG. 3 involving a stretch-resistant member.

In this variation, polymeric plug (125) is again slipped over the distal portion of core wire (110) and into the proximal portion of helical coil (120). The assembled joint is heated so to allow whatever thermoplastic that may be in polymeric insert (125) to flow and secure the detachable implant (120) to the core wire. Electrolytically severable joint (112) is also shown.

The major difference between this variation and others seen before is in the presence of coil (127) fixedly attached to stretch-resistant member (129). Of particular interest is the fact that coil (127) is soldered or preferably welded to detachable helical coil (120) in the region (131). Coil (127) should be made from a material similar to that of helical detachable coil (120) to prevent any untoward happenings during the severance of electrolytic joint (112) by provision of voltage couples or the like.

FIG. 8 shows still another variation of the invention of the invention in which a polymeric plug is used to separate the core wire (103) from the deployable implant (107). Incidentally, core wire (103) is shown to have an external marker (105) at its proximal end. Core wire (103) additionally has, adjacent detachment region (109), a surface (111) which is cut on a bias or at an angle to the axis of core wire (103). As is discussed in a number of prior patents assigned to Target Therapeutics Incorporated, this biased surface (111) enhances the physician's ability to detach the implantable device (107) from core wire (103) once electrolysis or electro-erosion is completed. This surface (111) is formed by use of a plug (113) which is typically polymeric in nature. A series of coils (115) and (117) are also shown in this variation. Coils (115) and (117) are typically produced of radiopaque material. They are positioned to allow easy visualization of the detachment region (109). The depiction found in FIG. 8 further has a shrink-wrapped coating (119) on the exterior of the device proximal of the detachment area (109).

In this instance, the proximal end of the implant (107), distal of the detachment zone (109) is constructed of a number of polymeric portions which allow for easy and practical assembly of the overall device. In particular, radiopaque coil (121) is surrounded by polymeric region (123). It is often the case that assembling the device shown in FIG. 8, the bare distal end of core wire (103) will first be wrapped with coil (121) and then the so-wrapped coil (121) will then be dipped in molten polymeric material to form the polymeric region (123). A polymeric plug, typically thermalplastic (125) is also inserted into the proximal end of implant (107). A polymeric coating, typically thermalplastic and typically a shrink-wrap is then placed over the two polymeric masses (123) and (125). Upon application of appropriate heat, outer covering (127) serves to attach the distal end of core wire (103) with the proximal end of implant (107). In many instances, the polymers used variously in region (123), region (125), and covering (127) are the same. Desirably, they are miscible with each other upon application of appropriate heat. It is also appropriate that they merely bind to each other in a well defined way.

This variation of the device is quite easy to assemble and the radiopaque coil (123) gives the physician-user a well defined end point for introduction of the implant (107) into the aneurysm or other cavity.

FIG. 9 shows a variation of the invention similar to that found in FIG. 8 except that it shows the use of a strain resistant vaso-occlusive device. For purposes of this description all of the core wire (103) proximal of detachment zone (109) is the same as is shown in FIG. 8. Similarly, the distal end of coil wire (103) includes a radiopaque coil (121) initially covered by a polymeric covering or region (123). In this instance, the polymeric region (131) placed within the proximal end of vaso-occlusive implant (107) includes a coil (133) having a distal loop (135) thereon. That distal loop is, in turn, attached to a stretch-resistant member (137) of the type discussed at length above with regard to FIG. 3. Again, this device may be assembled using a thermoplastic or shrink-wrap covering (139) placed exteriorly about polymeric region (123) and the proximal end of implant (107).

Figure 10:
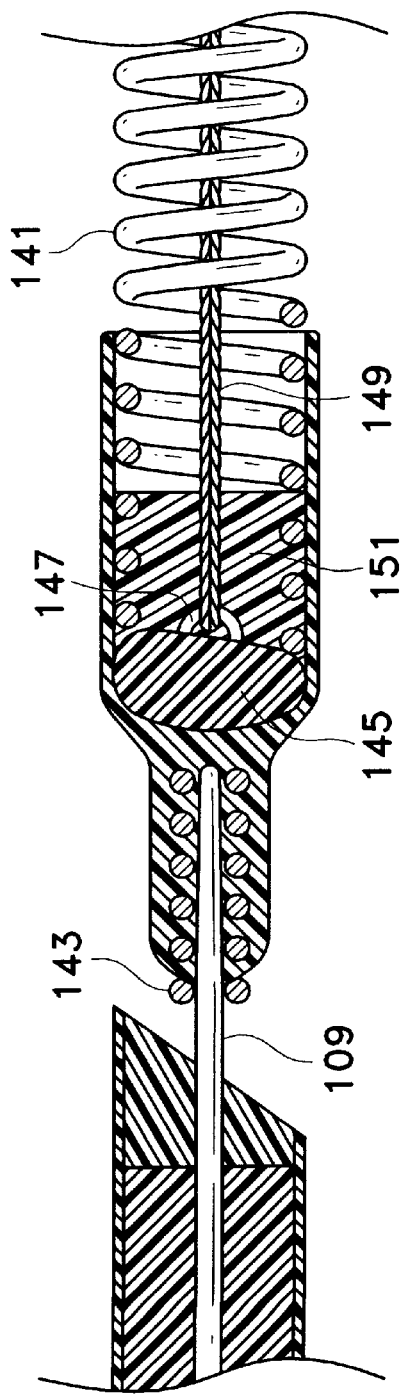
Figure 11:
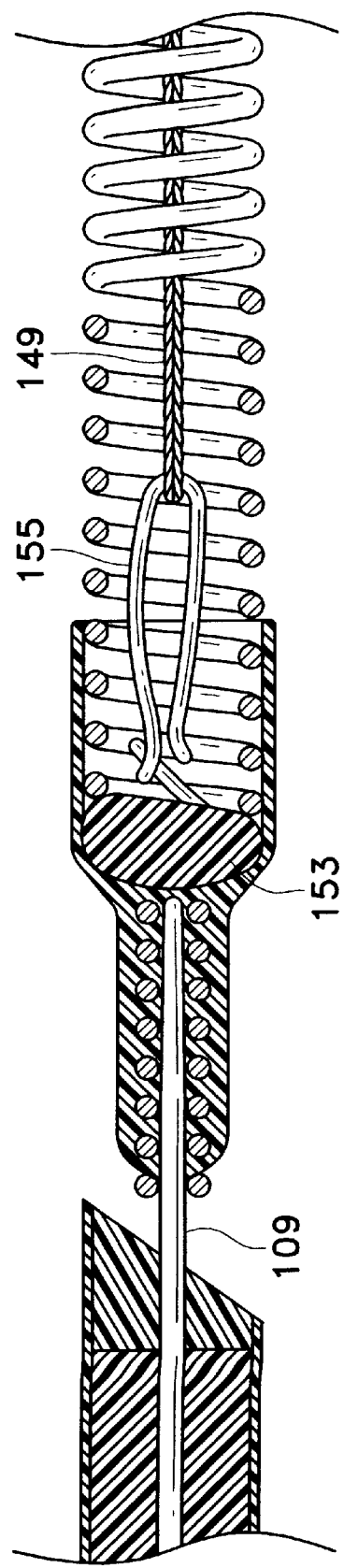

FIGS. 10 and 11 show still another variation of the insulative joint. In particular, FIG. 10 shows a implant (141) located distally of the region (109). In this instance, the distal end of the core wire has a radiopaque coil (143) wrapped around. Central to this variation of the invention is the presence of an anchoring member (145). Anchoring member (145) typically has a small loop (147) allowing for connection of the stretch-resistant member (149). It is desirable to include a polymeric region (151) distally of anchoring member (145). Polymeric region (151) may be placed in the implant (141) in such a way that it makes the stretch-resistant member (149) adhere well to the anchor member (145). Anchor member (145) should have a diameter which is larger than that of the interior of the implant (141) so that should the distal end of implant (141) be pulled strongly, the end of anchor member (145) not be able to pass through the lumen of implant member (141). Again, as with the variations shown in FIGS. 8 and 9, the exterior of the joint region shown in FIG. 10 may be all assembled using a polymeric tubing, preferably thermalplastic, which adheres to and joins all of the noted pertinent parts together.

FIG. 11 shows a similar variation of the anchor member (153) but is somewhat different in that the loop (155) for attaching to the strain resisting member (149) is larger and there is no polymeric region (151) as was shown in FIG. 10.

The variation shown in FIGS. 8 and 9 and especially those shown in FIGS. 10 and 11 are particularly useful when utilizing the insulating joint of this invention in combination with a very flexible vaso-occlusive coil as the implant. Such a highly flexible vaso-occlusive coil is described in U.S. Pat. Nos. 5,669,931 (Kupiecki et al.) and 5,690,666 (Berenstein et al.). The entirety of these patents is hereby incorporated by reference.

Figure 12:
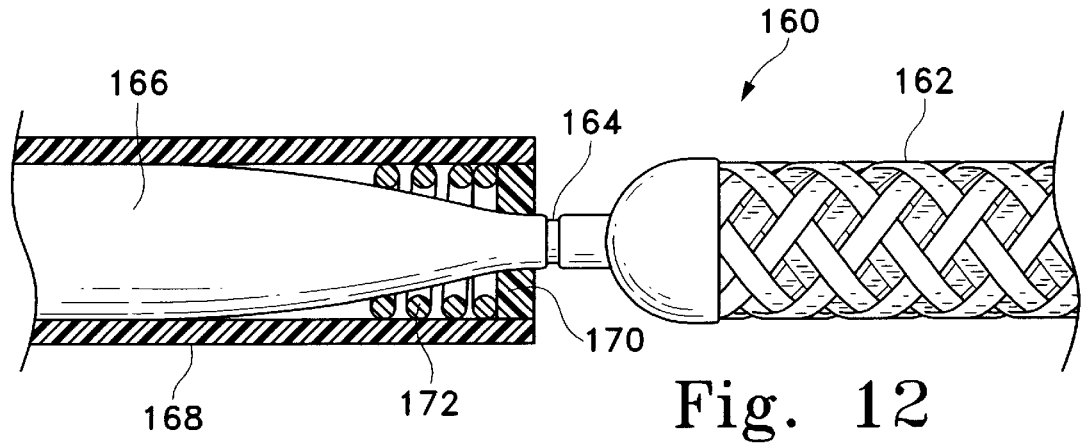
FIG. 12 shows a partial cross section of an electrolytic joint and a vaso-occlusive braid all made according to this invention.

Although the preferred variation of the invention is that found in the figures discussed above wherein a helical coil implant is fixably attached distally of electrolytically severable joint (112), other implants are suitable. For instance, FIG. 12 shows another variation of the inventive device (160) in which the implant is a vaso-occlusive braid (162), either woven or unwoven. The electrolytically severable joint (164) is shown proximally of vaso-occlusive braid (162). In this variation, the core wire is insulated with a tubular member (168) and a bushing (170). A stabilizing coil (172) is also depicted on the distal end of core wire (166). Bushing (170) and covering (168) serve to electrically insulate core wire (166) from the surrounding ionic fluid. These coverings along with the isolating joint. (not shown in cross section in this Figure) found on vaso-occlusive woven braid (162) apparently focus the electrolysis process on the electrolytically severable joint (164).

Figure 13:
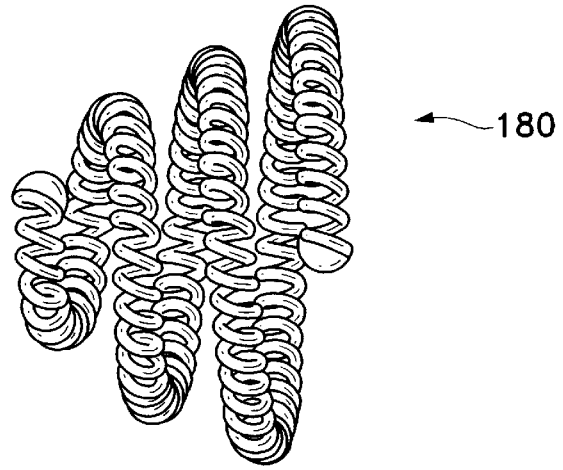
FIGS. 13 and 14 show helically wound vaso-occlusive coils having secondary shapes which may be deployed using the procedures described herein.
Figure 14:
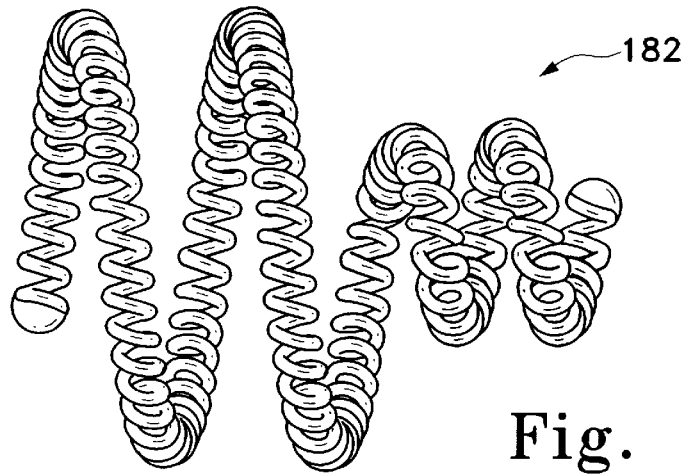

When the implant is a vaso-occlusive device, the shape of the device may be any of a number of suitable overall shapes to promote occlusion of the selected interior body space. In particular, when the implant is a helical coil, many shapes are known for treatment of particular abnormalities. FIGS. 13 and 14 show useful devices for treatment of arteriovenous malformations (AVM) and aneurysms. Specifically, FIG. 13 shows a vaso-occlusive coil (180) which has a secondary conical shape. A "secondary" shape is meant to include any form in which a wire is first formed into a first helical shape and that first helical shape is wound into a second shape which is, possibly, but not necessarily, helical. Secondary forms include generally spherical, ovoid, elongated, and any other form into which the device will "self-form" upon relaxation either within a body open region or simply outside the delivery catheter. As was noted above, vaso-occlusive devices are introduced through a catheter. Pushing the vaso-occlusive device through the catheter uses that first linear configuration which approximates the shape of the interior of the catheter. Secondary shape such as shown in FIGS. 13 and 14 are formed when the vaso-occlusive device is allowed to exit the distal end of the catheter. The secondary shape of the vaso-occlusive device (180) shown in FIG. 13 is, as noted just above, conical in form.

FIG. 14 shows a variation (182) of the inventive device in which two sections of the vaso-occlusive device have different secondary diameters.

Each of the vaso-occlusive devices described herein may also have attached fibrous materials to increase their thrombogenicity.

Figure 15:
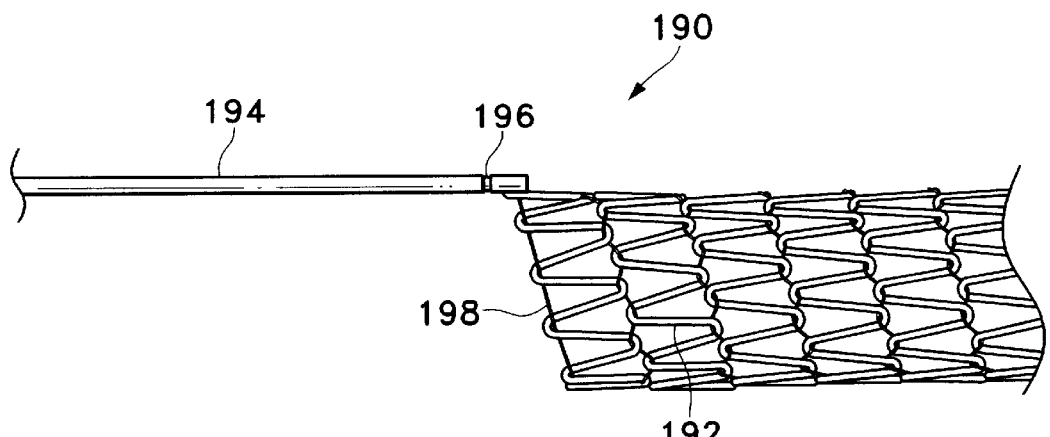
FIG. 15 shows a stent implant using the improvements of this invention.

FIG. 15 shows a variation (190) of the inventive device in which the implant is a stent (192). Core (194) is also is shown with an electrolytically erodable joint (196).

Figure 16:
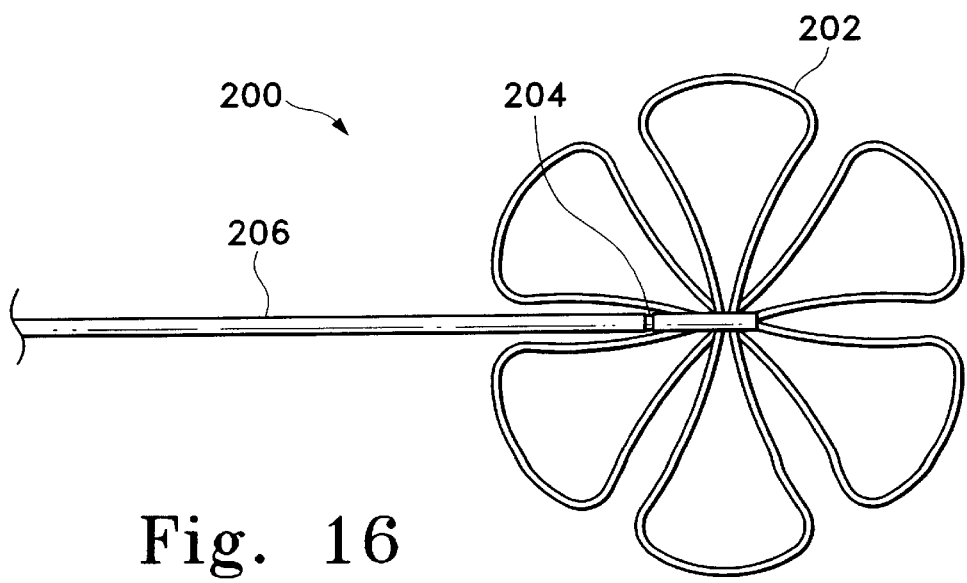
FIG. 16 shows a vena cava filter which may be deployed using the improvements of this invention.

The stent show in FIG. 15 is a variation of a self expanding stent typically made of a super-elastic alloy material, typically a nickel-titanium alloy (e.g., nitinol), that is well known in the art. The device has a zig-zag pattern of a metallic wire which is maintained in the noted and secondary form by a filament (198) which is woven through the bends of the stent to maintain the secondary shape. The primary shape is simply the shape shown but with a significantly lower diameter. The form of the stent is not important to the invention but is only illustrative of the form an implant may take FIG. 16 shows the expanded form of an implant (200) which may be used as a vena cava filter. Vena cava filters are well known in the art and are used to prevent the flow of blood clots distally in the vasculature. These blood clots would eventually be the site of occlusive strokes in the brain if allowed to travel distally. In any event, implant (200) shows the vena cava filter member (202), the electrolytically severable joint (204) and the push wire or core wire (206).

Figure 17A:
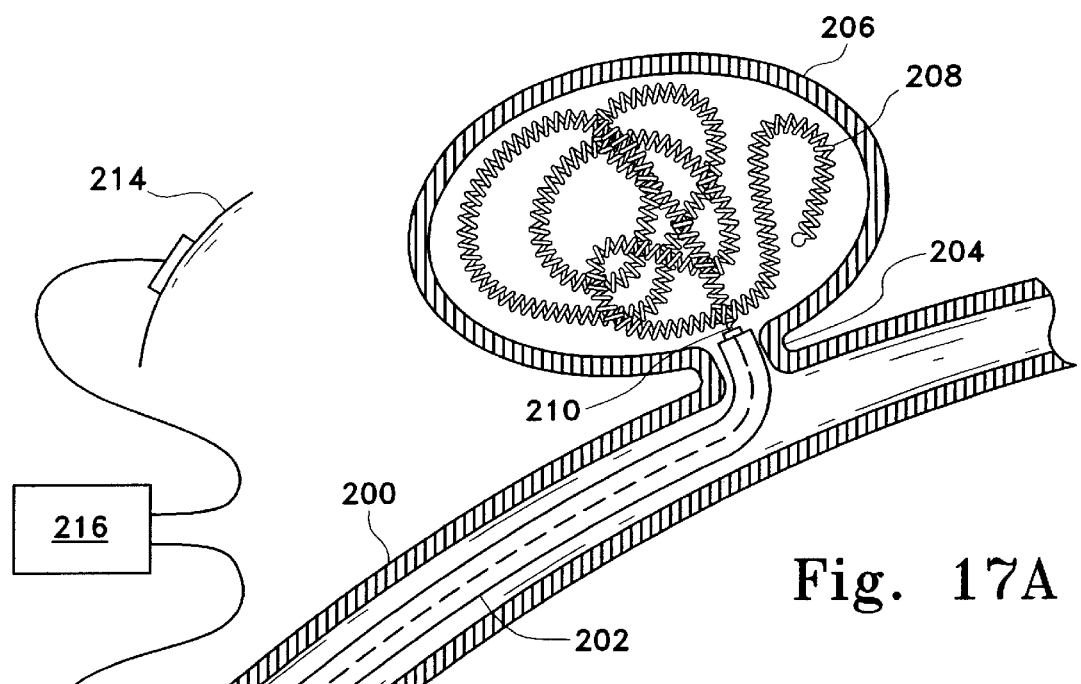
FIGS. 17A and 17B show, in schematic form, a procedure for deploying the inventive vaso-occlusive device of this invention.
Figure 17B:
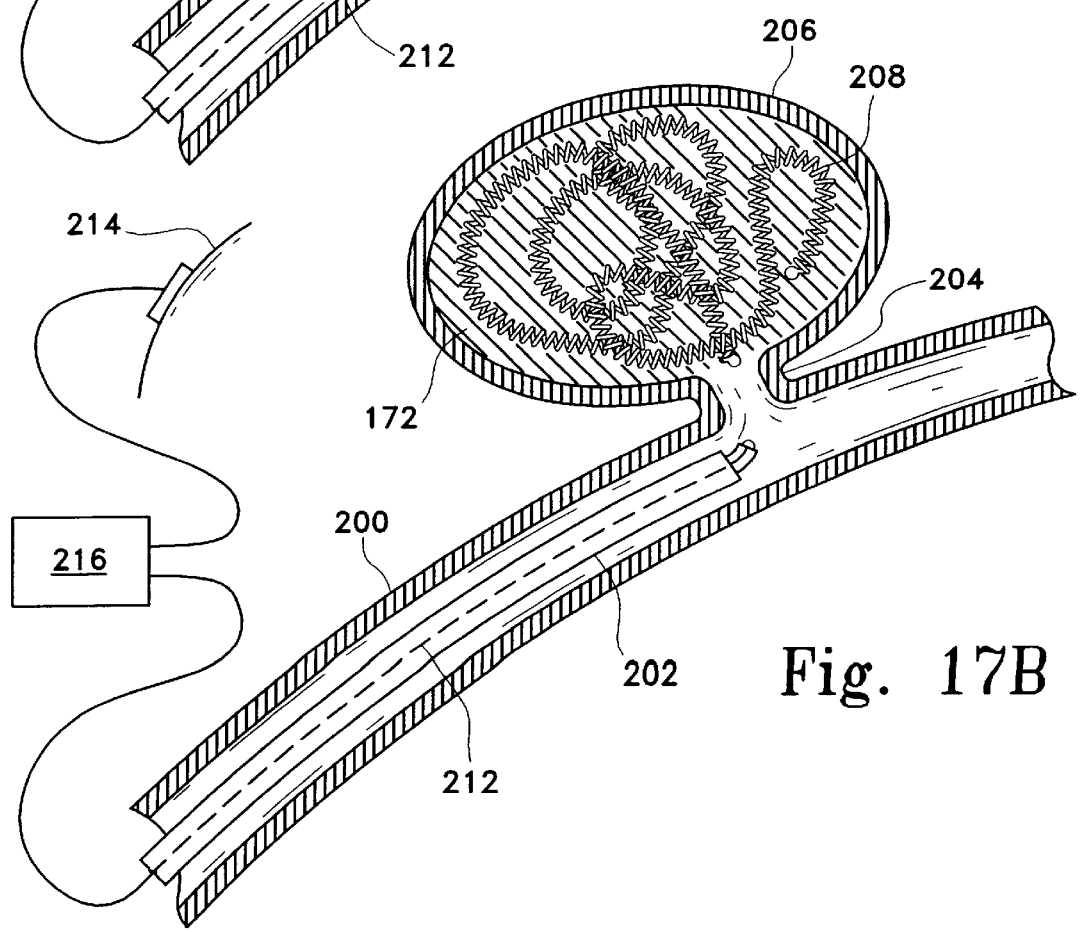

FIGS. 17A and 17B show placement of the inventive devices, specifically the vaso-occlusive variations of the invention, within the human body. FIG. 17A shows the placement within a vessel (200) with a tip of catheter (202) placed near aneurysm neck (204). The aneurysm itself is nominated (206). Vaso-occlusive device (208) is fed into aneurysm (206) at least until the sacrificial link or joint (210) (hidden within catheter (202) at this step) is exposed beyond the distal tip of catheter (202). A positive electric current of approximately 0.01–2 milliamps at 0.1–6 volts as applied to core wire (212). An embolic mass is then formed within aneurysm (206). The negative pole (214) of power supply (216) is typically placed in electrical contact with the skin so to complete the circuit. The vaso-occlusive device (208) is detached from core wire (212) by electrolytic disintegration of sacrificial link (210).

After sacrificial link (210) is at least mostly dissolved by electrolytic action, typically in less than two minutes and most often in less than one minute, the core wire (212), catheter (202), are removed from vessel (200) leaving aneurysm (206) occluded as represented by occlusion (218) in FIG. 17B.

This procedure is typically practiced under fluoroscopic control with local or general anesthesia. A transfemoral catheter may be used to treat cerebral aneurysm and is usually introduced at the groin. When the vaso-occlusive device (208) is isolated by a highly resistive material as is contemplated this invention, it is not affected by electrolysis. When the core wire (212) and the pertinent portions of the supporting coils at the distal tip of the core wire (when utilized) are adequately coated with insulating coverings, only the exposed portion of the sacrificial link (210) is affected by the electrolysis.

EXAMPLE

Figure 18:
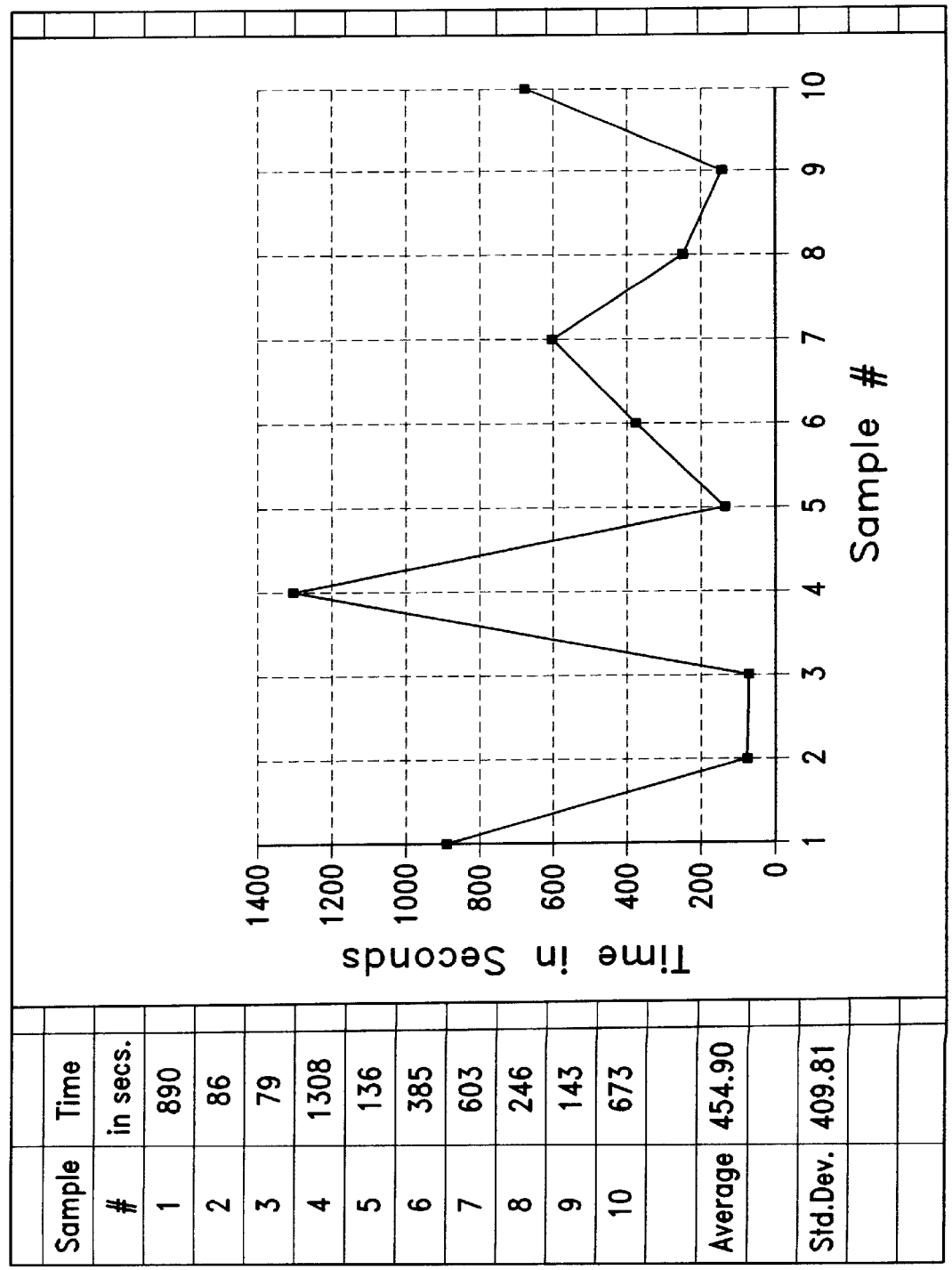
FIG. 18 is a graph of detachment times for a comparative commercial GDC device.

We compared detachment times for commercially available Guglielmi Detachable Coils (GDC) with those for a variation of the invention similar to that shown in FIG. 3. We constructed three sets of ten implant assemblies. The first set (FIG. 18) were commercial GDC assemblies as modified below. The second set (FIG. 19) had tantalum interior anchor coils ((136) in FIG. 3) and a distal hook (138) to which the stretch-resistant member (134) was attached. The third set (FIG. 16) were similar to those described in regard to FIG. 6 incorporating a PET insulator between the detachable coil and the electrolytic joint. The implants on each were platinum coils.

In the second set, the platinum bushing (140) was included and attached to the metallic center of the core wire (110). The assembly of tantalum interior anchor coil, platinum bushing, and core wire (110) was welded together.

To exaggerate and lengthen the detachment times for each set, as would be the case when an implant is inserted into an aneurysm already having a number of platinum coils with vestigal remaining stainless steel stubs remaining from prior detachments and having electrical contact with those coils, an additional stainless steel wire of about one inch length was added to the detachable coils. The resulting detachment times for the coils were increased by as much as ten-fold as is sometimes seen clinically.

Figure 19:
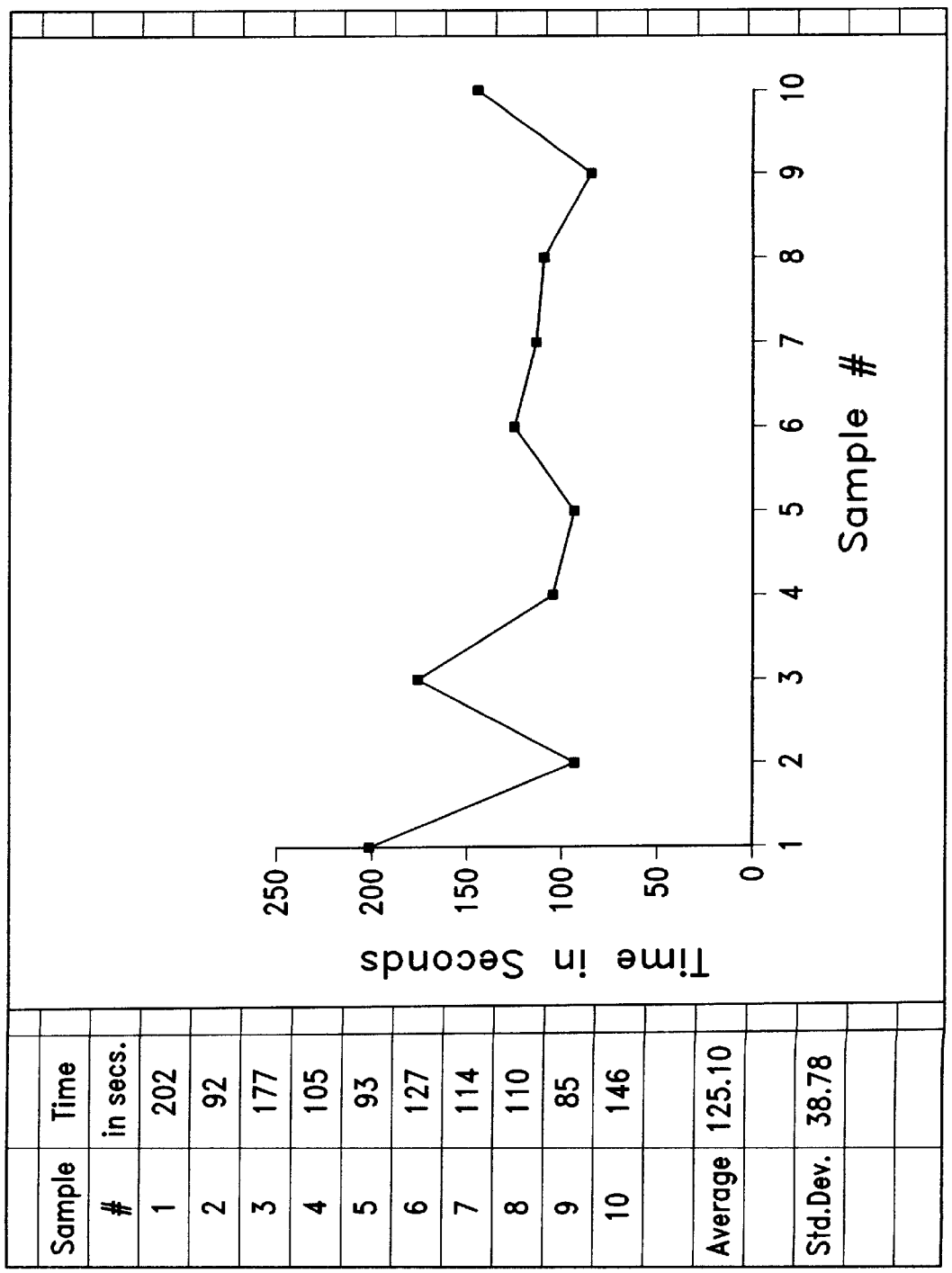
FIGS. 19 and 20 are graphs of detachment times for variations of the GDC device made according to the invention.
Figure 20:
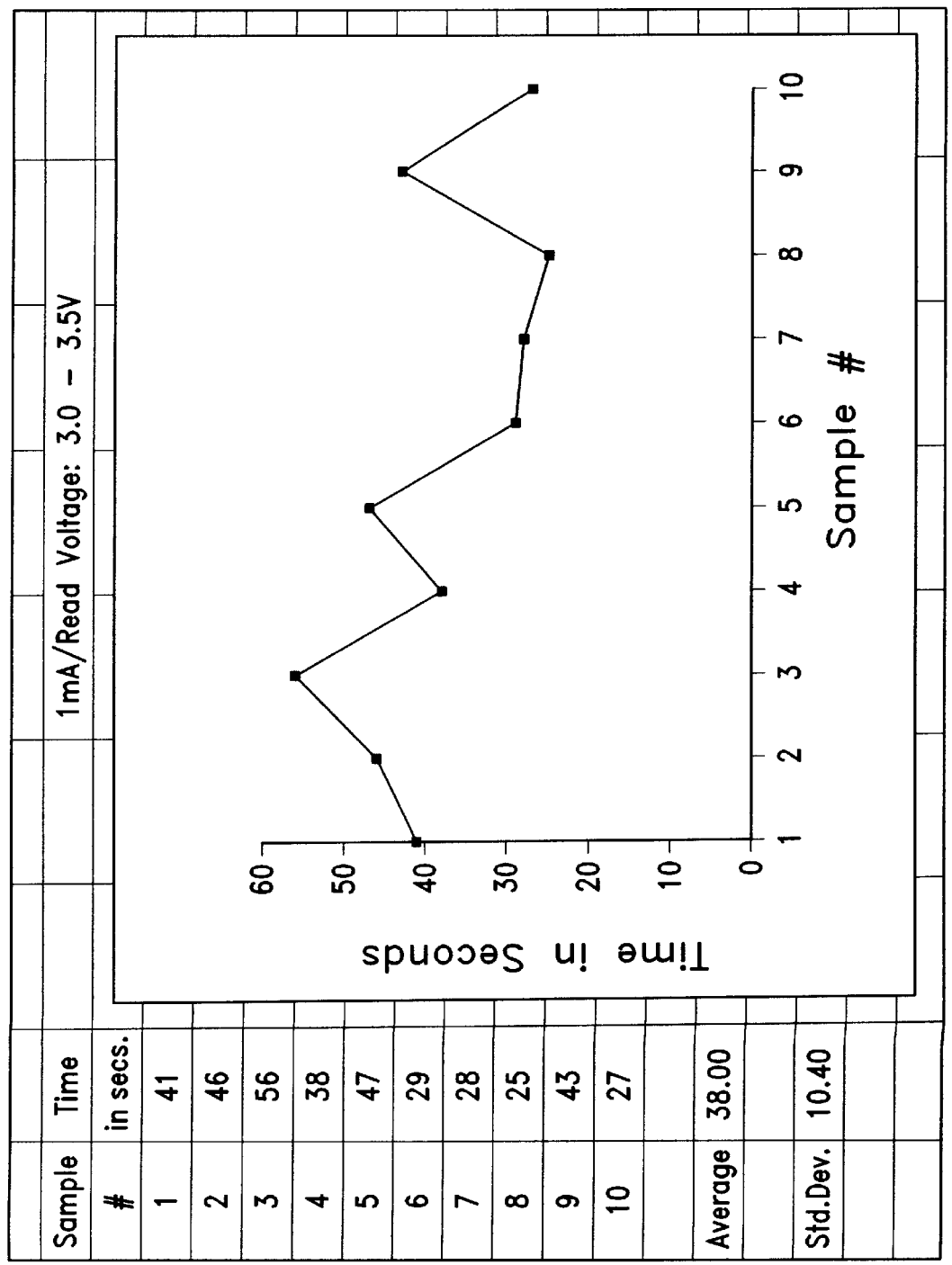

Each of the comparative commercial GDC's and the inventive variations were placed in a saline bath and subjected to a constant amperage of 1 ma and a resulting voltage of between 1.5 and 2.0 volts. The time for electrolytic erosion of the joint was measured. As shown in FIG. 14, the average time for detachment of the commercial GDC coil was 454.9 seconds. As shown in FIG. 19, the average time for detachment of the inventive variation GDC coil using tantalum insulator coils was 125.1 seconds. As shown in FIG. 20, the average time for detachment of the inventive variation GDC coil using a PET insulator sock was 38 seconds.

Many alterations and modifications may be made by those having ordinary skill in this art without departing from the spirit and scope of the invention. The illustrative embodiments have been used only for the purposes of clarity and should not be taken as limiting the invention as defined by the following claims.

What is claimed is:

1. An implant assembly for placement of an implant in the human body comprising:

(a) an implant member having a proximal end and a distal end, and (b) a wire having an electrolytically severable joint situated to release said implant member upon application of electrical energy to said electrolytically severable joint, said electrolytically severable joint being relatively more susceptible to electrolysis in an ionic solution than is said implant member, wherein a distal end of said wire is covered with a first insulative or highly resistive layer and said wire distal end is attached to said implant member proximal end by a second insulative or highly resistive layer, and wherein said implant member is electrically isolated from said electrolytically severable joint.

2. The implant assembly of claim 1 wherein said electrical isolation is due to at least one of said first or said second insulative or highly resistive layers.

3. The implant assembly of claim 2 wherein said first or said second insulative or highly resistive layer comprises tantalum oxide.

4. The implant assembly of claim 2 wherein said first or said second insulative or highly resistive layer comprises a polymer.

5. The implant assembly of claim 4 wherein said first or said second insulative or highly resistive layer comprises a thermoplastic.

6. The implant assembly of claim 4 wherein said first or said second insulative or highly resistive layer comprises a member selected from the group consisting of polyethylene, polypropylene, polyamides, and polyethyleneterephthalate.

7. The implant assembly of claim 2 wherein said first or said second insulative or highly resistive layer comprises an oxide-forming material.

8. The implant assembly of claim 1 wherein the implant member is a stent.

9. The implant assembly of claim 1 wherein the implant member comprises a vena cava filter.

10. The implant assembly of claim 1 wherein the implant member comprises a braid.

11. The implant assembly of claim 1 wherein the implant member comprises a helically wound coil.

12. The implant assembly of claim 11 further comprising a stretch-resistant member extending at least partially from said implant member proximal end to said implant member distal end.

13. The implant assembly of claim 12 wherein the stretch-resistant member comprises a member selected from the group consisting of polyethylene, polypropylene, polyamides, and polyethyleneterephthalate.

14. The implant assembly of claim 12 further including a helically wound coil situated proximally in the lumen of said helically wound implant member and fixedly attached to said stretch-resistant member.

15. The implant assembly of claim 14 wherein said helically wound coil situated proximally in the lumen of said helically wound implant member is welded to said helically wound implant member.

16. The implant assembly of claim 14 wherein said helically wound coil situated proximally in the lumen of said helically wound implant member additionally comprises a polymeric region.

17. The implant assembly of claim 16 wherein said helically wound coil situated proximally in the lumen of said helically wound implant member is fixedly attached to said stretch resistant member via a distal loop in said helically wound coil.

18. The implant assembly of claim 1 wherein said wire proximal end has a radio-opaque member placed thereon.

19. The implant assembly of claim 1 additionally comprising an insulative plug disposed in the implant member proximal end.

20. The implant assembly of claim 1 additionally comprising at least one proximal coil disposed on said wire proximal of said electrolytically severable joint.

21. The implant assembly of claim 20 additionally comprising a plug disposed on said wire adjacent said electrolytically severable joint and distal of said at least one proximal coil.

22. The implant assembly of claim 21 wherein a proximal insulative or highly resistive outer layer is at least partially disposed about said at least one proximal coil, and said plug.

23. The implant assembly of claim 1 additionally comprising a plug disposed on said wire proximal of said electrolytically severable joint.

24. The implant assembly of claim 23 wherein said plug comprises a polymer.

25. The implant assembly of claim 23 wherein said plug comprises a distal surface which is disposed at a non-perpendicular angle to an axis of said wire.

26. The implant assembly of claim 1 additionally comprising a distal coil disposed on said distal end of said wire and wherein said wire distal end and said distal coil are covered with said first insulative or highly resistive layer.

27. The implant assembly of claim 26 wherein said distal coil is radio-opaque.

28. A method for introduction of an implant into a space within a human body comprising:

1.) placing a delivery catheter distal tip near a selected space within the human body, 2.) introducing an implant assembly comprising:
   (a) an implant member having a proximal end and a distal end, and
   (b) a wire having an electrolytically severable joint situated to release said implant member upon application of electrical energy to said electrolytically severable joint, said electrolytically severable joint being relatively more susceptible to electrolysis in an ionic solution than is said implant member,
   wherein a distal coil is disposed on a distal end of said wire,
   wherein said wire distal end and said distal coil are covered with a first insulative or highly resistive layer,
   wherein said wire distal end is attached to said implant member proximal end by a second insulative or highly resistive layer, and
   wherein said implant member is electrically isolated from said electrolytically severable joint, into said catheter, 3.) placing said implant member into said selected space, and 4.) electrolytically detaching said implant member from said implant assembly.

29. An implant assembly for placement of an implant in the human body comprising:

(a) an implant member having a proximal end and a distal end, and (b) a wire having an electrolytically severable joint situated to release said implant member upon application of electrical energy to said electrolytically severable joint, said electrolytically severable joint being relatively more susceptible to electrolysis in an ionic solution than is said implant member, wherein a distal coil is disposed on a distal end of said wire, wherein said wire distal end is attached to said implant member proximal end by an insulative or highly resistive layer, and wherein said implant member is electrically isolated from said electrolytically severable joint.

30. The implant assembly of claim 29 wherein said electrical isolation is due to said insulative or highly resistive layer.

31. The implant assembly of claim 29 wherein said insulative or highly resistive layer comprises a polymer.

32. The implant assembly of claim 29 wherein said insulative or highly resistive layer comprises an oxide-forming material.

* * * * *